United States Patent [19]

Grahn Marisi

[11] Patent Number: 5,556,881
[45] Date of Patent: Sep. 17, 1996

[54] INSECT REPELLENT

[76] Inventor: Margaret R. Grahn Marisi, 45 Red Cedar Dr., Cranston, R.I. 02920

[21] Appl. No.: 390,440

[22] Filed: Feb. 16, 1995

Related U.S. Application Data

[63] Continuation of Ser. No. 76,107, Jun. 14, 1993, abandoned.

[51] Int. Cl.$^6$ .............................. A01N 37/00; A61K 31/00
[52] U.S. Cl. ............................ 514/557; 514/558; 514/724; 514/919; 424/DIG. 10
[58] Field of Search ..................... 424/195.1, DIG. 10; 514/73, 526, 558, 557, 919, 724

[56] References Cited

U.S. PATENT DOCUMENTS

| | | | |
|---|---|---|---|
| 1,871,949 | 8/1932 | Bottrell | 514/711 |
| 3,122,473 | 2/1964 | White et al. | 167/22 |
| 4,518,593 | 5/1985 | Juvin et al. | 424/195.1 |
| 5,227,163 | 7/1993 | Eini et al. | 424/195.1 |

OTHER PUBLICATIONS

Agricultural, Biology, Chemical, Nobuyuki Kurita et al, Jul. 21, 1982 at 67 "Synergistic Antimicrobial Effect of Ethanol, Sodium Chloride, Acetic Acid and Essential Oil Components".

Agricultural Biology, Chemical article, Nobuyuki Kurita et al, Jan. 18, 1982 at 1655, Synergistic Antimicrobial Effect of Acetic Acid, Sodium Chloride and Essential Oil Components.

Marcus, et al. J. Agric. Food Chem. 27(6): 1217–1223, 1979.

*Primary Examiner*—John W. Rollins
*Attorney, Agent, or Firm*—Barlow & Barlow, Ltd.

[57] ABSTRACT

An insect repellent and insecticide formulation for repelling and killing insects. The formulation includes a volume of water and essential ingredients of acetic acid and a limonene, particularly a mint extract.

1 Claim, No Drawings

INSECT REPELLENT

This is a continuation of application Ser. No. 08/076,107 filed on Jun. 14, 1993, abandoned.

BACKGROUND OF THE INVENTION

This invention relates to an insect repellent and insecticide, particularly for bees and wasps which contains acetic acid and an essential oil such as an edible plant oil soluble in ethyl alcohol or a limonene.

Insects breath by means of tubes which open at the body surface in spiracles. The tubes divide into very fine branches leading to all the organs. The spiracles are water repellant but oil may enter through them.

U.S. Pat. No. 1,871,949 discloses a composition of matter and the process of preparing it as an insect and rodent repellent. Specifically, this patent teaches the use of mixing oil of peppermint, sodium benzoate, sulphonethylmethane, animal glue, wood alcohol and water. This composition apparently hardens and sets on the material in which it is placed but it is not fully effective in repelling insects.

U.S. Pat. No. 3,122,473 discloses a composition of matter for repelling bees, consisting of acetic acid in an aqueous solution. This particular patent does not disclose the use of an essential oil.

Insecticides previously used have taken a variety of forms. Some have been oil based and in practically every case, they have contained chemical compositions which, in certain concentrations, can become harmful to the environment.

SUMMARY OF THE INVENTION

The primary object of the invention is to provide a material for use in repelling and killing insects which is inexpensive to manufacture, is easily sprayed and is non-injurious to plant and animal life.

I have discovered a composition of matter which includes certain ingredients which first changes the physiological behavior of the insect by upsetting its respiratory and ultimately all body systems of the insect. It repels and destroys the insect. Essentially the insecticidal and repellant composition consists of:

1. aqueous solution containing 4–8% by volume acetic acid
2. an essential oil in an ethyl alcohol solution A combination of 1 & 2 have a synergistic effect that destroys insects or repels them. This effect is determined by concentrations of formula. The essential oil, may be a hydrocarbon in the form of a derivative of limonene $C_{10}H_{16}$, that is present in many plant products such as orange oil, lemon peel, pine needles, peppermint and so forth. All of these components are used for human consumption and the solution is environmental safe and has a pleasant aroma.

DESCRIPTION OF THE PREFERRED EMBODIMENT

An aqueous solution containing 4–8% glacial acetic acid is commercially available in drug stores as vinegar ($CH_3COOH+H_2O$). It is theorized that the vinegar will upset the physiological balance of the insect and may also be effective in upsetting the circulatory system. Particularly when the vinegar is combined with limonene extract and particularly the mint extract which appears to be more effective, this mixture penetrates the spiracles causing an insult to the body systems of the insect which is incompatible with life. The oil acts as a carrier for the mixture to enable penetration through the spiracles.

Practice of the invention is illustrated by the following examples:

EXAMPLE 1

The solution I consisted of:

1 part aqueous solution 5% acetic acid;

3 part water; and 0.125 part oil of spearmint & peppermint in ethyl alcohol

A collection of 672 active honey bees were taken from a hive and placed in an 11.97 ml glass container with an 11.43 cm diameter opening. The container was covered with a cotton mesh to allow for ventilation. Some bees clustered at various areas of the container while others flew about. A great buzzing noise was audible from the container. The bees were then sprayed through the mesh opening with the named solution I. Within twenty seconds, most of the bees flew to the bottom of the container and after two minutes, forty seconds, two bees maintained flying ability. At three minutes, 22 seconds, only one bee was flying. At four minutes, none of the bees had flying ability. Buzzing noise remained strong. At six minutes, abdomens having rapid in-and-out movement (one hundred ten over a one minute count) exhibited great inability to walk and buzzing noise was less audible. All of the bees exhibited the same behavior, some sooner than others. Some attempted to fly but could only flap their wings. Some attempted to walk but could not hold themselves up and collapsed. They formed an almost perfect ring on the outer portion of the base of the container, piling up on one another. The stronger and more resilient went toward the center base and attempted normal activity. After fifty-two minutes, none of the bees were able to walk and many appeared dead. The active bees continued to crawl over one another, some still attempting to spread their wings. Prior to their death, they took a supine position, had rapid erratic movement of their extremities and curled the distal portion of their bodies inward once or twice. They gradually become more inactive and passive. Total cessation of all movement of the 672 bees took three and one-half hours.

EXAMPLE 2

A collection of 127 active honey bees were taken from a hive and placed in a 3.78 liter container with a 9.53 cm opening that was covered with cotton mesh to allow for ventilation. Twenty-five bees clung to the mesh covering, others clustered at various areas of the container. The named solution was sprayed through the mesh opening. The bees at the mesh opening rapidly dropped; some hanging on to one another forming a chain. All but seven bees dropped to the bottom of the container and exhibited the same behavior as described in Example 1. After twenty minutes, three bees remained at the mesh opening. After thirty minutes, one bee remained at the opening. After fifty minutes, the last bee dropped to the bottom of the container. Prior to death, all exhibited the same behavior as described in Example 1.

EXAMPLE 3

When named spray was used outdoors and sprayed directly at the Vespa (wasp, yellow jacket) and Apis (bee), they became disoriented and had erratic flying behavior. They were unable to fly straight, some dropping to the ground and others attempting to fly away. They seemed to communicate the danger to one another. Visible insects would not come near the sprayed area.

During the late summer, the Vespa (wasp, yellow jacket) were more aggressive, especially when humans would dine outside. They were more difficult to control so spraying became more effective when the dining or sitting area was sprayed prior to human use. When the spray solution was used in this manner, there seemed to be an invisible wall and when the Vespa (wasp, yellow jacket) or Apis (bee) would come close, the area seemed to have an invisible wall which made the insects fly away as soon as they came in contact with the sprayed area. Occasionally one or two bees or wasps would penetrate the sprayed area but would leave immediately when sprayed again, either by dropping or flying away. It was also noted in the open outdoor area that the spray was effective against other insects, including the mosquito which was effected in apparently the same manner in which the honey bees and yellow jackets were effected, although clinical studies were not conducted thereon.

EXAMPLE 4

One hundred thirty-eight (138) active bees were taken from a hive and were placed in a 3.78 ml. glass container with a 9.53 cm diameter opening that was covered with cotton gauze to allow ventilation. The bees were flying about. A loud buzzing noise was audible. The bees were mist sprayed once with a solution II:

1 part pure glacial acetic acid;

1 part oil of anise in ethyl alcohol; and 1 part $H_2O$.

After 5 seconds, bees were dropping and flying to base of container.

After 1 minute, eleven (11) of the bees were at the center of base of container. The remaining bees formed a ring at the outer aspects of the base of container and took a supine position.

After 2 minutes, all the bees were exhibiting the same pre-death behavior as described in Example Number 1.

After 3 minutes, all but six (6) of the bees appear dead. These six bees had slight movement of extremities.

After 9 minutes, two (2) bees continue slight movement of extremities.

After 10 minutes there was no movement. They had a shrivelled appearance. Death was instant for all but six of the bees. The anise mixture had a very pleasant aroma.

EXAMPLE 5

One hundred twenty-seven (127) honey bees were taken from a hive and placed in a 3.78 ml. glass container with a 9.53 cm diameter opening that was covered with cotton gauze to allow ventilation. The bees were loudly buzzing and flying about. Solution III consisted of:

10 cc of sesame oil was blended with;

10 cc of 70% solution of $C_2H_5OH$.

There was a slight separation of the mixture.

This mixture was further blended with 10 cc 5% acetic acid and 10 cc of $H_2O$.

The mixture, while not foul smelling, did not have a pleasant aroma. The bees were mist sprayed with Solution III.

After 2 minutes, all bees remain active. Six (6) bees remain at top of container at gauze opening.

After 3 minutes, bees were sprayed a second time. Two remain at top of container. Most remain active. One bee attempting to fly. All bees have rapid erratic movement.

After 7 minutes, two (2) bees remain at gauze of container opening. One (1) bee was attempting to fly.

After 8 minutes, one (1) bee at container opening.

After 9 minutes, no bees at top of container. Buzzing noise less audible. The bees formed a ring at outer aspects of base of container. After 10 minutes faint buzzing noise audible.

After 12 minutes, two (2) bees attempting to walk.

After 13 minutes none of the bees attempting normal activity.

After 15 minutes movement decreasing.

After 20 minutes ring formation at base of container unchanged. All of the bees appear to be dying. All are in supine position exhibiting the same pre-death behavior as described in Example Number 1.

After 30 minutes many appear dead.

After 36 minutes the bees appear to be shrivelling, all in a supine position.

Slight audible buzzing noise.

After 61 minutes, one (1) bee attempted to fly.

After 90 minutes, eight (8) bees have slight movement. One (1) bee attempted to walk. All others are dead.

EXAMPLE 6

One hundred twenty-one (121) active honey bees were taken from a hive and placed in a glass 3.78 ml. container with a 9.53 cm diameter opening that was covered with cotton gauze to allow ventilation. Loud buzzing noise was audible. Bees were then sprayed with Solution IV:

1 part of oil of lemon in ethyl alcohol; and 1 part glacial acetic acid. Within five (5) minutes the buzzing noise decreased. Some bees attempted flying. Bees were mist sprayed a second time. Fourteen (14) minutes later, bees had formed a ring at base of container and exhibited the same behavior prior to death as described in Example Number 1. After 41 minutes all bees were dead.

EXAMPLE 7

One hundred twenty-eight (128) active honey bees were taken from a hive and placed in a 3.78 ml. glass container with a 9.53 cm diameter opening that was covered with cotton gauze to allow ventilation. Loud buzzing sound was audible. The bees were then sprayed with Solution V:

50% pure mint and pure peppermint extract (essential oils in ethyl alcohol solution) and 50% $H_2O$.

After 3 minutes, loud buzzing noise was audible and some bees attempted to fly. After 5 minutes buzzing continued. Activity slowed, but all bees are active. After 1 minute activity resumed. Within 30 minutes bees actively flying about.

EXAMPLE 8

One hundred twenty-one (121) active honey bees were taken from a hive and placed in a 3.78 ml. glass container that was covered with cotton gauze to allow ventilation. Bees were then sprayed with Solution VI:

1.0 cc of pure glacial acetic acid;

1 cc oil of peppermint in 89% ethyl alcohol/water solution;

30 cc of $H_2O$.

After spraying bees, noise remained loud. All the bees were active, none were flying, some were falling to base of container.

After 1 minute, bees were given three mist sprays. All bees were active, crawling on all areas of jar making a great humming noise; none are grouped together.

After 3 minutes some bees are clustering on bottom of container.

After 5 minutes, more bees dropped to base of container. Noise very audible. Bees continue to drop, cluster, and crawl over one another, remaining active. Many remain at top of container opening clinging to gauze.

After 10 minutes bees were again sprayed.

After 13 minutes, more bees clustering at base grouping together at left of base, some bees flying.

After 15 minutes all bees continue to have active movement.

After 20 minutes, bees seem to have some recovery.

After 24 minutes bees were given 10 mist sprays.

After 25 minutes, all but eleven (11) bees were at the base of container.

After 26 minutes, fifteen (15) bees actively climbing sides of container; none are flying. Seven (7) bees remain at top of container; buzzing noise decreasing.

After 29 minutes most of bees at base of container, crawling over one another.

After 30 minutes, five (5) bees at top of container clinging to cotton gauze.

After 34 minutes, one (1) active bee at top of container, buzzing audible, some bees attempting to fly.

After 36 minutes, one (1) bee flying and one (1) bee remaining at cotton gauze.

After 38 minutes, seven (7) bees attempting to crawl up sides of container.

After 39 minutes, bees clustering in an oval formation at container base and up one side of container.

After 40 minutes, zero (0) bees at top of container.

After 41 minutes, ten mist sprays were given.

After 46 minutes all bees clustered together. One bee attempting to fly.

After 54 minutes, three (3) bees attempting activity. All remaining bees clustered at base.

After 55 minutes, two (2) bees attempting activity.

After 57 minutes, four (4) bees away from group attempting normal activity.

After 64 minutes, eight (8) bees left cluster and attempted activity. Bees were given 10 mist sprays. One bee attempted flying, nine (9) bees attempting activity. All other bees clustered on half of base of container.

After 1 hour 17 minutes, one (1) bee attempting great activity, two (2) bees attempting activity. All other bees forming smaller clusters.

After 1 hour 22 minutes, clustering in two groups at base of container-some attempting to leave their cluster and trying to attempt normal activity.

After 1 hour 25 minutes, seven (7) bees attempting activity, they remained clustered at base, many have movement.

After 1 hour 38 minutes, seven (7) bees still attempting activity, remaining bees have little movement. One bee is flying.

After 1 hour 55 minutes, the bees are gradually making recovery. Bees are moving and clustering up side of container.

After 6 hours bees becoming more active with greater attempt at normal activity. No bees appear dead.

After 9 hours 30 minutes all bees have fully attained and resumed normal activity, flying about and buzzing loudly.

EXAMPLE 9

One hundred fifty-three (153) active honey bees were taken from a hive and placed in a 3.78 ml. glass container with 9.53 diameter opening which was covered with cotton gauze to allow ventilation. Solution VII:

1 cc pure olive oil was dissolved in 5 cc of 190% proof pure $C_2H_5OH$.

This mixture was further combined with 5 cc pure glacial acetic acid and 200 cc of $H_2O$.

The bees were then sprayed with Solution VII.

After 1 minute all bees sat in the base of container.

After 4 minutes, five (5) bees returned to top of container.

After 6 minutes bees have less activity, very audible buzzing noise.

After 10 minutes, two (2) bees at top of container. Remaining bees formed two clusters at base of container. Noise less audible.

After 17 minutes, one bee attempted flying. Many attempting to spread wings.

After 25 minutes exhibiting less activity. One bee flying. Twelve bees are now in one cluster, remaining bees had clustered at opposite side of container. Eight bees are attempting activity.

After 34 minutes, six bees are attempting activity. Two bees attempting to fly in short spans.

After 35 minutes bees were sprayed again. Fourteen bees attempted to climb opposite side of container where bees are clustered.

After 45 minutes, all bees clustered on one side of container. Two bees attempting activity. One bee attempting to fly.

After 1 hour 10 minutes, three bees appeared dead in supine position, exhibiting the same pre-death behavior as described in Example Number 1.

After 1 hour 20 minutes, all bees completely immobilized, all grouped together at outer aspects of base of container having very little movement.

After 4 hours 40 minutes, three bees died. All remaining 150 bees resumed normal activity, flying about and buzzing loudly.

Bees were then placed outside to fly away. Some bees did not leave container. Some flew away and three bees died after leaving container.

EXAMPLE 10

Approximately 90 active honey bees were taken from a hive and were placed in a 3.78 ml glass container that was covered with cotton gauze to allow for ventilation.

The following solution was used for this experiment:

30 parts $H_2O$ 1 part pure mint extract 1 part pure glacial acetic acid

Bees were mist sprayed with this solution. Many of the bees flew to the base of the container. Many bees clung to gauze at the top of the container. Bees remained active at base of container. None flying.

After 1 minute, three additional mist sprays were given. Bees very active, crawling over all areas of container. Audibly loud buzzing. None of the bees grouped.

After 3 minutes, some bees were clustered at the base of the container. None are flying.

After 5 minutes, bees continue to drop from cotton gauze covering to the base of the container. Many still remain clinging to cotton gauze.

After 10 minutes, bees were mist sprayed again.

After 14 minutes, more bees clustering at one side of base. More of the bees are grouped together. Some flying activity.

After 20 minutes, bees are having some recovery.

After 30 minutes, recovery activity increasing. Ten (10) mist sprays given through mesh gauze. All but nine (9) bees flew and fell to the base of container. Grouping and crawling over one another.

After 50 minutes, no bees at top of container. One bee attempting to fly. Two bees attempting activity.

After 1 hour, bees are clustered and quiet. Three bees away from others—attempting normal activity. No flying ability.

After 1 hour 30 minutes, one bee flying.

After 1 hour 55 minutes, bees gradually starting to recover.

Bees moving in a cluster up one side of glass container.

After 2 hours 30 minutes, bees becoming more active. Normal activity increasing. None of the bees appear dead.

After 3 hours 30 minutes, all of the bees have recovered. Flying about container, buzzing loudly. Normal activity resumed.

The initial spray of this solution repelled the bees. Additional sprays immobilized them. Bees were taken outside to fly away. Two bees stayed initially in the glass container; three bees flew out of container to the ground and died. The remaining bees flew into the environment.

EXAMPLE 11

One hundred twenty-four (124) active honey bees were taken from a hive and placed in a 3.78 ml glass container with an opening of 9.53 cm that was covered with cotton gauze to allow for ventilation. Bees very active, buzzing loudly and flying about glass container.

Bees were mist sprayed once with a mixture of:

1 part pure mint extract 1 part pure glacial acetic acid 1 part water

Within five (5) seconds, bees dropped and flew to the base of container forming a ring at the outer aspects of container. All of the bees took a supine position.

After 1 minute 50 seconds, all of the bees were exhibiting pre-death behavior.

After 2 minutes 45 seconds, five (5) bees have slight movement of their extremities; remaining bees appear dead.

After 4 minutes, three (3) bees continue to have slight movement of extremities.

After 8 minutes, all movement had ceased. All of the bees had a shriveled appearance.

With one mist spray of above described solution, death was instant for all but five (5) bees, who maintained slight movement.

What is claimed is:

1. An insecticidal composition to be used by humans for repelling winged flying insects consisting of by volume 20–30% aqueous solution 4–8% acetic acid 0.2–0.4% oil of anise 2.6–3.6% alcohol

70–80% $H_2O$.

\* \* \* \* \*